(12) United States Patent
Liu et al.

(10) Patent No.: US 11,985,993 B2
(45) Date of Patent: May 21, 2024

(54) ULTRASOUND-ELECTRODE-NANO-POROUS MEMBRANE COUPLING HYDROGEN PRODUCTION AND STERILIZATION SYSTEM

(71) Applicant: ZHEJIANG UNIVERSITY, Hangzhou (CN)

(72) Inventors: Donghong Liu, Hangzhou (CN); Enbo Xu, Hangzhou (CN); Jianwei Zhou, Hangzhou (CN); Hao Wang, Hangzhou (CN); Tian Ding, Hangzhou (CN); Huan Cheng, Hangzhou (CN); Xingqian Ye, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 621 days.

(21) Appl. No.: 17/272,654

(22) PCT Filed: May 20, 2020

(86) PCT No.: PCT/CN2020/091171
§ 371 (c)(1),
(2) Date: Mar. 2, 2021

(87) PCT Pub. No.: WO2021/000662
PCT Pub. Date: Jan. 7, 2021

(65) Prior Publication Data
US 2021/0337833 A1 Nov. 4, 2021

(30) Foreign Application Priority Data
Jul. 3, 2019 (CN) .......................... 201910595760.4

(51) Int. Cl.
A23L 2/54 (2006.01)
A23C 3/07 (2006.01)
(Continued)

(52) U.S. Cl.
CPC ................ *A23L 2/54* (2013.01); *A23C 3/073* (2013.01); *A23C 3/085* (2013.01); *A23C 9/1522* (2013.01);
(Continued)

(58) Field of Classification Search
CPC .... C25B 1/04; C02F 1/36; B01J 19/10; A23L 2/54; A23C 3/073; A61L 2/025
See application file for complete search history.

(56) References Cited

FOREIGN PATENT DOCUMENTS

| CN | 204661480 U | 9/2015 |
|---|---|---|
| CN | 109097790 A | 12/2018 |

(Continued)

*Primary Examiner* — Ciel P Contreras

(57) ABSTRACT

The present invention discloses an ultrasound-electrode-nano-porous membrane coupling hydrogen production and sterilization system, which comprises a vessel and a plurality of hydrogen production units arranged in the vessel. The hydrogen production unit comprises a cavity, and a broadband ultrasonic generator and a circular hydrogen production electrode located in the cavity. The circular hydrogen production electrode wraps around the broadband ultrasonic generator. A bottom membrane at the bottom of the cavity is hydrophobic at the inner side and hydrophilic at the outer side, and a side membrane of the cavity is hydrophilic at the inner side and hydrophobic at the outer side and is mounted vertically or obliquely upwards by an angle of 0-45 degrees. The system has the functions of continuously and efficiently facilitating self-circulation micro-flow of a liquid system, hydrogen dissolution (as nano-bubbles), conversion from the interface to the bulk phase and dispersion of bubbles, sterilization and others.

4 Claims, 2 Drawing Sheets

(51) Int. Cl.
*A23C 3/08* (2006.01)
*A23C 9/152* (2006.01)
*A23L 2/44* (2006.01)
*A23L 2/50* (2006.01)
*A61L 2/025* (2006.01)
*B01J 19/10* (2006.01)
*C02F 1/36* (2023.01)
*C25B 1/04* (2021.01)
*C25B 9/00* (2021.01)

(52) U.S. Cl.
CPC .................. *A23L 2/44* (2013.01); *A23L 2/50* (2013.01); *A61L 2/025* (2013.01); *B01J 19/10* (2013.01); *C02F 1/36* (2013.01); *C25B 1/04* (2013.01); *C25B 9/00* (2013.01); *A23V 2002/00* (2013.01)

(56) References Cited

FOREIGN PATENT DOCUMENTS

| | | |
|---|---|---|
| CN | 110367426 A | 10/2019 |
| JP | 2007105677 A | 4/2007 |
| TW | 200932687 A | 8/2009 |
| WO | 2016171483 A1 | 10/2016 |

ULTRASOUND-ELECTRODE-NANO-POROUS MEMBRANE COUPLING HYDROGEN PRODUCTION AND STERILIZATION SYSTEM

TECHNICAL FIELD

The present invention relates to the technical field of liquid food processing, and particularly to a unit combination system for generating hydrogen-rich nanobubbles and a method for preparing antibacterial functional beverages using the unit combination system.

BACKGROUND

With the increasing development of hydrogen science, the insight into and demand for hydrogen, human health, medical treatment, and diet grow higher and higher. Hydrogen is the simplest, smallest, and most widely distributed element in nature. As early as in 2007, a Japanese scientist discovered the selective anti-oxidation ability of hydrogen, which led to the active research by many scholars. Hydrogen has the characteristics of strong penetrating ability and fast diffusion rate, and it can enter any part of the body to exert an anti-oxidation, anti-inflammatory, anti-apoptotic and other effects. Compared with other commonly used food-grade antioxidants (such as vitamin C, and polyphenols, etc.), hydrogen has a simple structure, and the reaction product thereof is simple, harmless, and easy to be excreted without residue. Moreover, hydrogen can selectively bind to reactive/toxic reactive oxygen radicals without destroying other important active oxygen signaling molecules.

Hydrogen is often used in the preparation of a hydrogen-rich liquid, especially hydrogen-rich water. However, in the prior art, the type of hydrogen-rich liquid beverages is simple, the method of dissolving hydrogen comprises mainly hydrogen filling and high-pressure solubilization. Especially for beverage systems with ions and dissolved substances, the dissolved hydrogen content is generally low (0.2-2.2 ppm), the volume of dissolved hydrogen is large (visible bubbles or micron-sized bubbles are observed), hydrogen bubbles rise and break easily, and have poor stability. Hydrogen production by simple electrolysis and chemical reactions tends to produce by-products, causing secondary pollution to the liquids. This greatly affects the anti-oxidation, antibacterial and health care functions, as well as high-quality generous flavours and diversified types of hydrogen-rich beverages. Recent studies have found that dissolving a gas in water in nano-scale size gives rise to an over-saturation dissolution rate and bubble stabilization that cannot be explained by the macroscopic principle (Henry's law). Particularly, on a hydrophobic surface, nano bubbles can exist for a long time stably due to the micro-interfacial tension, surface energy, and nano-effect of nano-bubbles. Therefore, the traditional and existing preparation methods for hydrogen-rich beverages urgently need to be scientifically upgraded to meet the growing multi-directional demand of consumers for hydrogen-rich beverages that are healthy and delicate.

SUMMARY

To solve the defects in the prior art, an object of the present invention is to provide an ultrasound-electrode-nanoporous membrane coupling hydrogen production and sterilization system. The system can conveniently, intelligently and greenly generate hydrogen-rich nanobubbles with a diameter of 20-1000 nm. The dissolved hydrogen (3-6 ppm) rises slowly and can exist stably for more than 8-36 hrs in an unsealed state. The anti-oxidation and antibacterial functions of the prepared hydrogen-rich beverages are remarkable, and the flavours are richer and more generous than previous beverages.

In order to achieve the above objects, the specific technical solutions adopted in the present invention are as follows:

An ultrasound-electrode-nanoporous membrane coupling hydrogen production and sterilization system includes a vessel, and a plurality of hydrogen production units arranged in the vessel. The hydrogen production unit includes a cavity, and a broadband ultrasonic generator and a circular hydrogen production electrode located in the cavity. The circular hydrogen production electrode wraps around the broadband ultrasonic generator. A bottom membrane at the bottom of the cavity is hydrophobic at the inner side and hydrophilic at the outer side; and a side membrane is hydrophilic at the inner side and hydrophobic at the outer side and is mounted vertically or obliquely upwards by an angle of 0°-45°. The membrane assembled self-circulation system can not only form hydrogen nanobubbles, but also prevent large particles and macromolecules in the liquid from entering the reaction environment, promote hydrogen enrichment and diffusion, and avoid secondary pollution by reaction byproducts. The top cover is made of an airtight material.

Further, the bottom membrane is made of non-toxic materials such as nano-scale (<1000 nm pore diameter) ceramics, fibers, and metal-organic frameworks.

Further, the broadband ultrasonic generator is adjustable in a range including, without limitation, 20 KHz to 400 KHz, and is located at the center of the reactor to radiate waves to the surroundings.

Further, a hydrogen tester is installed at a water outlet of the system tank.

The present invention has the following beneficial effects. The ultrasound-electrode-nanoporous membrane coupling hydrogen production and sterilization system of the present invention has the functions of continuously and efficiently facilitating self-circulation micro-flow of a liquid system, hydrogen dissolution (as nano-bubbles), conversion from the interface to the bulk phase and dispersion of bubbles, sterilization and others. The hydrogen content in a prepared anti-bacterial functional beverage is high (3-6 ppm), where the diameter of hydrogen-rich nano-bubbles is distributed within the range of 20-1000 nm, and the nano-bubbles are retained for 8-36 hrs or more even in an unsealed state. The anti-oxidation and antibacterial functions of the prepared hydrogen-rich beverages are remarkable, and the flavours are richer and more generous than previous beverages. The system of the present invention is simple, intelligent and efficient, the product is high in quality and green and has a health care function, waste of a lot of filled hydrogen and high-pressure energy consumption are avoided, secondary pollution of the system is prevented in processing, and food-grade requirements are met.

In the figures, 1. broadband ultrasonic generator, 2. circular hydrogen-production electrode, 3. food-grade nanoporous side membrane, 4. food-grade nanoporous bottom membrane, 5. top cover, 6. nanobubbles at the interface, 7. nanobubbles in the bulkphase, 8 vessel, 9. feeding port, 10. discharging port, 11. liquid circulating hydrogen dissolving pipe

DESCRIPTION OF THE EMBODIMENTS

Figure 1:
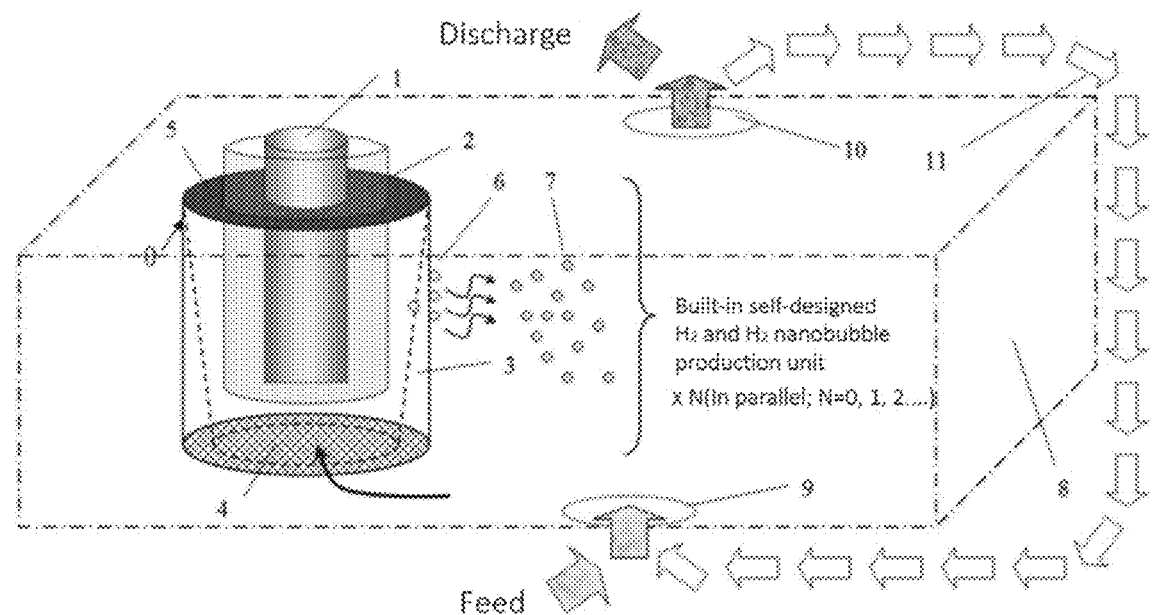
FIG. 1 shows a microcirculation system and its box design for producing hydrogen nanobubbles by coupling ultrasound-electrode-nanoporous membranes according to the present invention.
Figure 3:
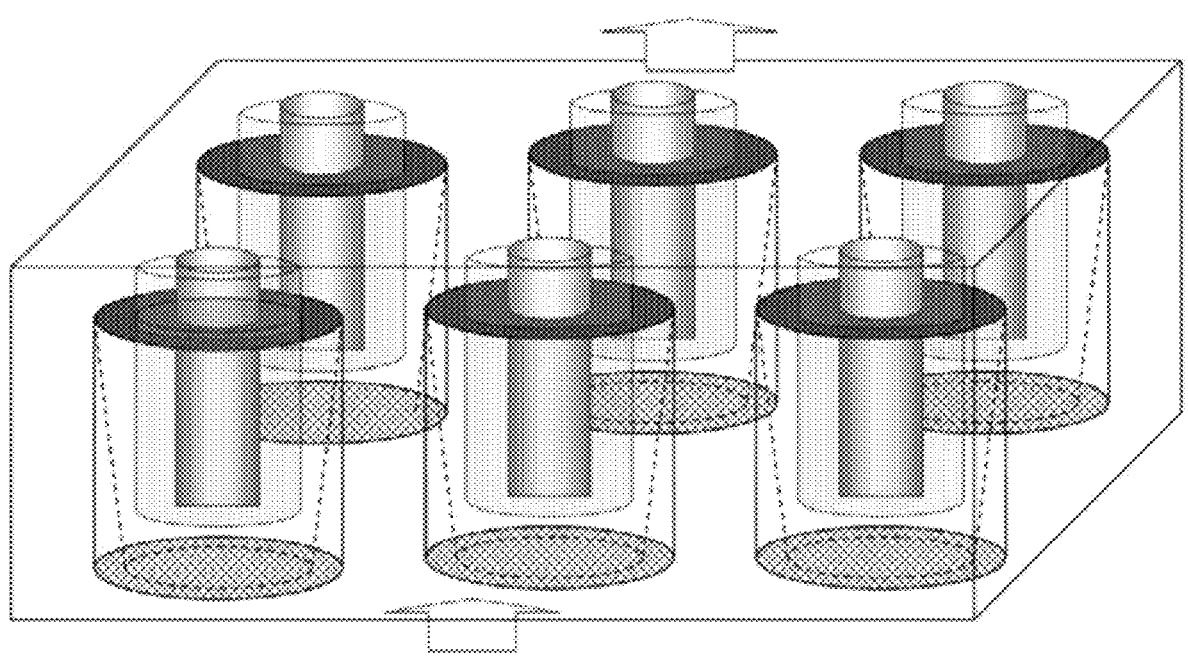
FIG. 3 shows a hydrogen-production microsystem array used in the present invention.

As shown in FIGS. 1 and 3, an ultrasound-electrode-nanoporous membrane coupling hydrogen production and sterilization system includes a vessel 8 and a plurality of hydrogen production units arranged in the vessel 8. The hydrogen production unit includes a cavity, and a broadband ultrasonic generator 1 and a circular hydrogen-production electrode 2 located in the cavity. The circular hydrogen-production electrode 2 wraps around the broadband ultrasonic generator 1. A bottom membrane 4 at the bottom of the cavity is hydrophobic at the inner side and hydrophilic at the outer side; and a side membrane 3 is hydrophilic at the inner side and hydrophobic at the outer side and is mounted vertically or obliquely upwards by an angle of 0°-45°. The inclined angle is beneficial to extending the production process of nanobubbles in the bulk phase and further reducing the bubble diameter. The membrane assembled self-circulation system can not only form hydrogen nanobubbles, but also prevent large particles and macromolecules in the liquid from entering the reaction environment, promote hydrogen enrichment and diffusion, and avoid secondary pollution by reaction byproducts. The top cover is made of an airtight material.

Figure 2:
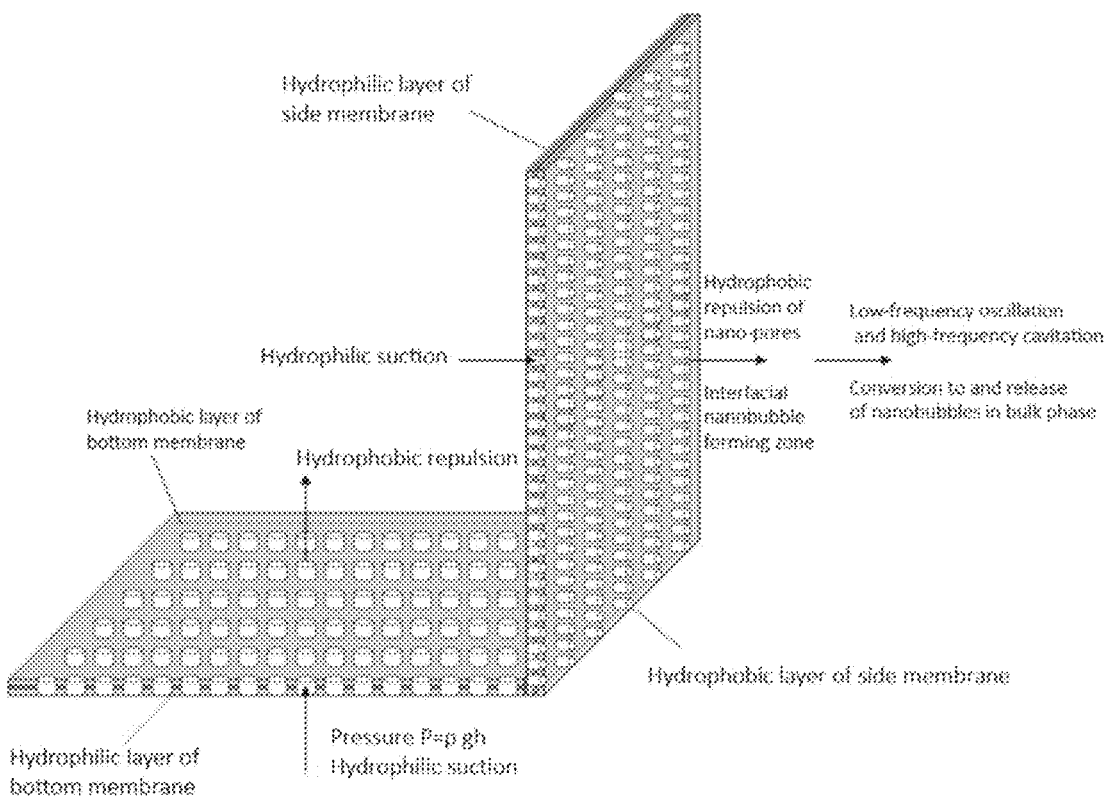
FIG. 2 is an illustration of a nanoporous membrane and a process associated therewith used in the present invention.

In use, the liquid is introduced from the vessel 8 until it fills the entire vessel 8 and covers the hydrogen production unit. As shown in FIG. 2, the liquid enters the hydrogen production unit through the bottom membrane 4 that is hydrophobic at the inner side and hydrophilic at the outer side and reacts to produce hydrogen under the action of the circular electrode 2. When a large amount of hydrogen is enriched on the side membrane 3, the circular electrode 2 is turned off. The broadband ultrasonic generator 1 is controlled to cause a linear oscillation and cavitation effect on the hydrogen-liquid mixed system, which cooperates with the porous membrane to form hydrogen nanobubbles at the interface that gradually transform into 20-1000 nm hydrogen nanobubbles in the bulk phase. The hydrogen nanobubbles in the bulk phase pass through the inside hydrophilic and outside hydrophobic membranes of the side membrane 3 of the hydrogen production unit, and enter the vessel 8 again to complete the hydrogen dissolution. Moreover, due to the difference in density, the hydrogen-rich nanobubble containing liquid tends to rise slightly, and the hydrogen-rich nanobubble free liquid sinks slightly, and will enter the hydrogen production unit again under the action of water pressure (P=ρgh, where the larger the density ρ of the liquid beverage is and the greater the distance h from the bottom membrane to the liquid surface is, the larger the flow-promoting pressure P will be) and the suction of the membrane, to form the circulating hydrogen dissolution in the microchannel, thus achieving the large and uniform hydrogen dissolution in the liquid. After hydrogen is produced for a certain period of time, the water outlet on the upper part of the tank is opened to discharge and package the hydrogen-rich liquid.

In the entire hydrogen production process, the heat generated by the circular electrode 2 needs to be controlled below 30° C. The lower the temperature is, the larger the filling gap between water molecules and the stronger the hydration will be, which is beneficial to the hydrogen production and dissolution balance. The broadband ultrasonic generator is adjustable in a range including, without limitation, 20 KHz to 400 KHz, and is located at the center of the reactor to radiate waves to the surroundings. Without additional high pressure, a low frequency promotes the growth of nanobubbles is promoted at; the diffusion of the nanobubbles at the interface is protected by the oscillation of the hydrophobic membrane on the outer surface of the side membrane; and a high frequency promotes the formation of gas burst and cavitation in the liquid and assists the mass generation of nanobubbles in the bulk phase. Further, the liquid introduced from the bottom membrane 4 of the hydrogen production unit generates hydrogen under the action of the electrode, and then the hydrogen is formed into 20-1000 nm hydrogen nanobubbles under the action of short-term low-frequency-high-frequency alternating ultrasound (5-20 min) cooperated with the porous membrane, thus reducing clusters with water molecules and mixing and diffusion with them.

Moreover, in the hydrogen production process, the energy release from ultrasonic cavitation and bursting of some bubbles and the microjet effect can quickly sterilize the liquid. After packaging, the hydrogen-rich nanobubbles (with an internal high pressure that is 3-30 kPa or above according to the Young-Laplace equation) further continue to sterilize the beverage by means of long-term micro-release during storage.

Further, a hydrogen tester can be installed at the water outlet of the system tank to detect in real time whether the hydrogen content in the liquid at the outlet meets the standard (3-6 ppm), and the material is discharged when the standard is reached.

Further, the bottom membrane is made of non-toxic materials such as nano-scale (<1000 nm pore diameter) ceramics, fibers, and metal-organic frameworks, etc., which facilitates the penetration of water, intercepts the entry of foreign matter in the liquid, and promotes the leaching out of reaction byproducts. The hydrogen-production electrode can be a noble metal (such as Pt), a non-noble metal (such as Mg), and a glass carbon electrode. The by-products in the reaction process are purified and blocked by the membrane, which avoids the contamination of beverages and enhances the safety compared with traditional electrolysis.

The system of the present invention is applicable to such food systems as pure-phase water, mineral water, diluted fruit juice (with or without fruit grains), milk, alcohol and other liquids, and to most liquid beverages and health beverages. The present invention will be described in detail by way of examples below. The following examples are provided for illustration rather than limiting the scope of the present invention.

The raw materials used in the following examples are all commercially available products. The production equipment used for processing is a self-designed ultrasound-electrode-nanoporous membrane coupling microsystem. The dissolved hydrogen level and hydrogen nanobubbles are measured by a hydrogen tester or commonly used methods.

EXAMPLE 1

Pure water was introduced from the port at the bottom of the tank until it filled the entire reaction tank and covered the hydrogen production unit. The liquid entered from the porous membrane at the bottom of the hydrogen production unit and reacted to generate hydrogen under the action of the circular electrode. At this time, the temperature was controlled at 0° C. When hydrogen was abundantly enriched and penetrated through the nanoporous metal membrane (pore size 200 nm; θ=45°) on the side of the microreactor, the circular electrode was turned off, and the broadband ultrasonic generator (20 KHz low frequency for 5 min; 400 KHz high frequency for 15 min) was controlled to cause a linear oscillation and cavitation effect on the hydrogen-liquid mixed system, so as to form hydrogen nanobubbles (about 300 nm) at the interface that gradually transform into hydrogen nanobubbles (about 50 nm) in the bulk phase. The energy release from ultrasonic cavitation and bursting of some bubbles and the microjet effect can quickly sterilize the pure water. The water outlet on the upper part of the tank was opened to discharge the hydrogen-rich water (6 ppm, where the bubbles remained stable for at least 24 h in an unsealed state).

EXAMPLE 2

Mineral water was introduced from the port at the bottom of the tank until it filled the entire reaction tank and covered the hydrogen production unit. The liquid entered from the porous membrane at the bottom of the hydrogen production unit and reacted to produce hydrogen under the action of the electrode. At this time, the temperature was controlled at 5° C. When hydrogen was abundantly enriched and penetrated through the nanoporous fiber membrane (pore size 100 nm; θ=30°) on the side of the microreactor, the electrode was turned off, and the ultrasonic generator (50 KHz low frequency for 3 min; 400 KHz high frequency for 10 min) was controlled to cause a linear oscillation and cavitation effect on the hydrogen-liquid mixed system, so as to form hydrogen nanobubbles (about 150 nm) at the interface that gradually transform into hydrogen nanobubbles (about 20 nm) in the bulk phase. The energy release from ultrasonic cavitation and bursting of some bubbles and the microjet effect can quickly sterilize the mineral water. The water outlet on the upper part of the tank was opened to discharge the hydrogen-rich mineral water (4 ppm, where the bubbles remained stable for at least 36 h in an unsealed state).

EXAMPLE 3

The juice was introduced from the port at the bottom of the tank until it filled the entire reaction tank and covered the hydrogen production unit. The liquid entered from the porous membrane at the bottom of the hydrogen production unit and reacted to generate hydrogen under the action of the electrode. At this time, the temperature was controlled at 30° C. When hydrogen was abundantly enriched and penetrated through the nanoporous ceramic membrane (pore size 1000 nm; θ=15° on the side of the microreactor, the electrode was turned off and the ultrasonic generator (20 KHz low frequency for 5 min; 200 KHz high frequency for 5 min) was controlled to cause a linear oscillation and cavitation effect on the hydrogen-liquid mixed system, so as to form hydrogen nanobubbles (about 1000 nm) at the interface that gradually transform into hydrogen nanobubbles (about 800 nm) in the bulk phase. The energy release from ultrasonic cavitation and bursting of some bubbles and the microjet effect can quickly sterilize the juice. The water outlet on the upper part of the tank was opened to discharge the hydrogen-rich juice (3 ppm, where the bubbles remained stable for at least 8 h in an unsealed state).

EXAMPLE 4

The milk was introduced from the port at the bottom of the tank until it filled the entire reaction tank and covered the hydrogen production unit. The liquid entered from the porous membrane at the bottom of the hydrogen production unit and reacted to generate hydrogen under the action of the electrode. At this time, the temperature was controlled at 0° C. When hydrogen was abundantly enriched and penetrated through the nanoporous metal membrane (pore size 500 nm; θ=0°) on the side of the microreactor, the electrode was turned off and the ultrasonic generator (30 KHz low frequency for 2 min; 300 KHz high frequency for 8 min) was controlled to cause a linear oscillation and cavitation effect on the hydrogen-liquid mixed system, so as to form hydrogen nanobubbles (about 550 nm) at the interface that gradually transform into hydrogen nanobubbles (about 300 nm) in the bulk phase. The energy release from ultrasonic cavitation and bursting of some bubbles and the microjet effect can quickly sterilize the milk. The water outlet on the upper part of the tank was opened to discharge the hydrogen-rich milk (3.5 ppm, where the bubbles remained stable for at least 12 h in an unsealed state).

COMPARATIVE EXAMPLE 1

Pure water was introduced from the port at the bottom of the tank until it filled the entire reaction tank and covered the hydrogen production unit. The liquid entered from the porous membrane at the bottom of the hydrogen production unit and reacted to generate hydrogen under the action of the circular electrode. At this time, the temperature was controlled at 0° C. When hydrogen was abundantly enriched (where no side membrane is provided), the circular electrode was turned off, and the broadband ultrasonic generator (20 KHz low frequency for 5 min; 400 KHz high frequency for 15 min) was controlled to cause a linear oscillation and cavitation effect on the hydrogen-liquid mixed system, so as to form a certain level of dissolved hydrogen. The energy release from ultrasonic cavitation and bursting of some bubbles and the microjet effect can quickly sterilize the pure water. The water outlet on the upper part of the tank was opened to discharge the hydrogen-rich pure water (0.6 ppm, where the bubbles remained stable for no more than 20 min in an unsealed state).

Compared with the hydrogen-rich water prepared without the side membrane in the comparative example, in the examples, due to the micro-interfacial tension, surface energy, and nano-effect of the nano-bubbles on the hydrophobic surface, the nano-bubbles have an over-saturation dissolution rate. The hydrogen content in the hydrogen-rich water prepared in the examples is significantly increased, and the bubbles can be present persistently and stably. In the present invention, a self-designed ultrasound-electrode-nanoporous membrane coupling microcirculation system for producing hydrogen nanobubbles is adopted, with which hydrogen-rich (3-6 ppm) nanobubbles with a diameter of 20-1000 nm that can exist stably for 8 to 36 hrs or more even in an unsealed state can be conveniently, intelligently and greenly produced, and with which the hydrogen-rich beverage prepared has significant antioxidant and antibacterial functions, diversified varieties, richer and more generous flavours, thus having great commercial prospects.

In summary, the present invention has been described in detail through the above general description and specific examples, but some improvements or enhancements can be made in the hydrogen production unit and beverage production of the present invention, which are obvious to those skilled in the art and also fall within the scope of protection of the present invention.

What is claimed is:

1. An ultrasound-electrode-nano-porous membrane coupling hydrogen production and sterilization system, comprising a vessel and a plurality of hydrogen production units arranged in the vessel, wherein a hydrogen production unit comprises a cavity, and a broadband ultrasonic generator and a circular hydrogen production electrode located in the cavity, the circular hydrogen production electrode wrapping around the broadband ultrasonic generator; a bottom membrane at a bottom of the cavity is hydrophobic at an inner side and hydrophilic at an outer side, and a side membrane of the cavity is hydrophilic at the inner side and hydrophobic at the outer side and is mounted vertically or obliquely upwards at an angle of 0-45 degrees from a vertical direction; and a top cover is made of an airtight material.

2. The system according to claim 1, wherein the bottom membrane is made of nano-scale ceramics, fibers, metal-organic frameworks, or other non-toxic materials.

3. The system according to claim 1, wherein the broadband ultrasonic generator is adjustable in a range including, without limitation, 20 KHz to 400 KHz, and is located at a center of a reactor to radiate waves to surroundings.

4. The system according to claim 1, wherein a hydrogen tester is installed at a water outlet of a tank of the system.

* * * * *